(12) United States Patent
Jordan et al.

(10) Patent No.: US 9,120,807 B2
(45) Date of Patent: Sep. 1, 2015

(54) THIENOPYRIMIDINE COMPOUNDS

(75) Inventors: Allan Jordan, Winnersh (GB); Simon Bedford, Winnersh (GB); Klenke Burkhard, Winnersh (GB); Ian Yule, Winnersh (GB); Karine Poullennec, Winnersh (GB)

(73) Assignee: Vernalis (R&D) Ltd., Winnersh, Berkshire (GB)

( * ) Notice: Subject to any disclaimer, the term of this patent is extended or adjusted under 35 U.S.C. 154(b) by 736 days.

(21) Appl. No.: 12/678,378

(22) PCT Filed: Sep. 19, 2008

(86) PCT No.: PCT/GB2008/003173
§ 371 (c)(1),
(2), (4) Date: Jun. 24, 2010

(87) PCT Pub. No.: WO2009/037463
PCT Pub. Date: Mar. 26, 2009

(65) Prior Publication Data
US 2011/0118284 A1    May 19, 2011

(30) Foreign Application Priority Data
Sep. 21, 2007  (GB) ................................... 0718434.4

(51) Int. Cl.
*C07D 495/04*  (2006.01)
*A61K 31/519*  (2006.01)

(52) U.S. Cl.
CPC ............. *C07D 495/04* (2013.01); *A61K 31/519* (2013.01)

(58) Field of Classification Search
CPC ............................... C07D 95/04; A61K 31/519
USPC ........................... 514/260.1; 544/278; 549/50
See application file for complete search history.

(56) References Cited

FOREIGN PATENT DOCUMENTS

WO          0102409 A     1/2001

OTHER PUBLICATIONS

Vippagunta et. al., Advanced Drug Delivery Reviews, 2001, Elsevier, vol. 48, pp. 3-26.*
International Search Report for PCT/GB2008/003173 dated Nov. 3, 2008.

* cited by examiner

*Primary Examiner* — Sarah Pihonak
(74) *Attorney, Agent, or Firm* — Banner & Witcoff, Ltd.

(57) ABSTRACT

Compounds of formula (I) are $A_{2B}$ receptor antagonists, wherein $R_1$ is optionally substituted aryl or an optionally substituted 5- or 6-membered heteroaryl ring; $R_2$ and $R_3$ are independently selected from hydrogen, $C_1$-$C_6$ alkyl, $C_3$-$C_8$ cycloalkyl, $C_3$-$C_8$ cycloalkyl-($C_1$-$C_6$)-alkyl, aryl-($C_1$-$C_6$)-alkyl optionally substituted in the ring part thereof, a 5- or 6-membered monocyclic heterocyclic group optionally linked via a $C_1$-$C_6$ alkylene chain and optionally substituted in the ring part thereof, benzimidazol-2-yl-methyl, pyrid-3-yl-carbonyl, or (1-methyl-piperidin-4-yl)-carbonyl-methyl; or $R_2$ and $R_3$ taken together with the nitrogen atom to which they are attached form an optionally substituted 5- or 6-membered ring; $R_4$ is $C_1$-$C_3$ alkyl, $C_2$-$C_3$ alkenyl, —N(—$R_5$)—$R_6$, or optionally substituted heteroarylmethylamino; and $R_5$ and $R_6$ are independently selected from hydrogen or $C_1$-$C_3$ alkyl; or $R_5$ and $R_6$ taken together with the nitrogen atom to which they are attached form an optionally substituted 4- to 6-membered saturated ring.

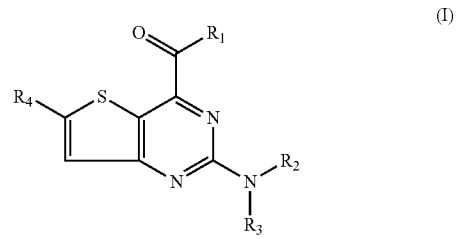

25 Claims, No Drawings

THIENOPYRIMIDINE COMPOUNDS

CROSS REFERENCE TO RELATED APPLICATIONS

This application is a National Stage application of co-pending PCT application PCT/GB2008/003173 filed Sep. 19, 2008, which claims the benefit of Great Britain application number 0718434.4 filed Sep. 21, 2007. These applications are incorporated herein by reference in their entireties.

This invention relates to novel thienopyrimidine derivatives having $A_{2B}$ receptor antagonistic activity, to the use of such compounds in medicine, in relation to the treatment of disorders which are responsive to antagonism of the $A_{2B}$ receptor such as nociception, asthma, COPD, inflammatory disorders, diabetes, diabetic retinopathy and cancer, and to pharmaceutical compositions containing such compounds.

BACKGROUND TO THE INVENTION

Adenosine is a naturally occurring purine nucleoside, the effects of which include stimulation of nociception afferents, bronchconstriction, immunosupression, vasodilation, inhibition of platelet aggregation, cardiac depression and inhibition of neurotransmitter release.

Adenosine produces a wide range of pharmacological effects mediated by activation of specific cell surface receptors, which are members of the G-protein coupled receptor family. Four subtypes of adenosine receptors have been identified, designated $A_1$, $A_{2A}$, $A_{2B}$ and $A_3$.

The $A_{2B}$ adenosine receptor subtype is coupled to the $G_s$ G-protein and stimulates adenylyl cyclase activity. Although significant advancement has been made in the understanding of the molecular pharmacology and physiology of $A_{2B}$ adenosine receptors, due to the lack of highly potent and selective ligands for this receptor subtype, many questions about the patho-physiological role of $A_{2B}$ receptors are yet to be resolved (Feoktistov and Biaggioni, Pharmacological Reviews (1997), 49(4), 381-402).

$A_{2B}$ receptors have been implicated in:
(i) the regulation of mast cell secretion (Feoktistov and Biaggioni., Journal of Clinical Investigation (1995), 96(4), 1979-86).
(ii) pain (Abo-Salem et al., Journal of Pharmacology and Experimental Therapeutics (2004), 308(1), 358-366).
(iii) inflammation (Yang et al., Journal of Clinical Investigation (2006), 116(7), 1913-1923).
(iv) cancer (Zeng et al., Drug Development Research (2003), 58(4), 405-411).
(v) diabetes (Harada et al., Journal of Medicinal Chemistry (2001), 44(2), 170-179).
(vi) gene expression (Boyle et al., Arthritis & Rheumatism (1996), 39(6), 923-930).
(vii) cell growth (Dubey et al., Hypertension (1996), 27(3 Pt 2), 786-93 Hypertension (1996), 27(3 Pt 2), 786-93, Dubey et al., Hypertension (1998), 31(1 Pt 2), 516-21).
(viii) intestinal functions (Murthy et al., Journal of Neurochemistry (1995), 64(1), 77-84).
(ix) neurosecretion (Mateo et al., 1995).
(x) vascular tone (Haynes et al., American Journal of Physiology (1995), 268(5, Pt. 2), H1862-H1868).
(xi) asthma (Feoktistov et al., Trends in pharmacological sciences (1998), 19(4), 148-153; Holgate, British Journal of Pharmacology (2005), 145(8), 1009-1015).
(xii) COPD (Van den Berge et al., Drugs in R&D (2007), 8(1), 13-23).

Thus, there remains a medical need for low molecular weight selective antagonists of the $A_{2B}$ receptor with pharmacokinetic and pharmacodynamic properties making them suitable for use as pharmaceutical agents. There also remains a medical need for new treatments of disorders mediated by the $A_{2B}$ receptor, by selective antagonism of the $A_{2B}$ receptor, particularly the treatment of nociception, asthma, COPD, inflammatory disorders, diabetes, diabetic retinopathy and cancer. The object of the present invention is to provide such pharmaceutical agents and treatments.

It has now been found that certain thienopyrimidine derivatives show efficacy as selective $A_{2B}$ antagonists.

BRIEF DESCRIPTION OF THE INVENTION

Our co-pending international patent application no. PCT/GB00/02517 is concerned with a class of thieno- and furopyrimidine derivatives which are antagonists of the adenosine $A_{2A}$ receptor. This invention relates to a subset of compounds within the PCT/GB00/02517 class, but which are not specifically disclosed therein.

The present invention relates to a class of substituted thienopyrimidine compounds useful as selective $A_{2B}$ antagonists, for example, for the treatment of nociception, asthma, COPD, inflammatory disorders, diabetes, diabetic retinopathy and cancer. A core thieno-pyrimidine bicyclic ring, with substitution on the thieno portion by an amino group, and substitution on the pyrimidine portion by a (hetero)aryl-carbonyl group in addition to an amino group, are principle characterising features of the compounds with which the invention is concerned.

DETAILED DESCRIPTION OF THE INVENTION

According to the present invention, there is provided a compound of formula (I) or a pharmaceutically acceptable salt, hydrate or solvate thereof:

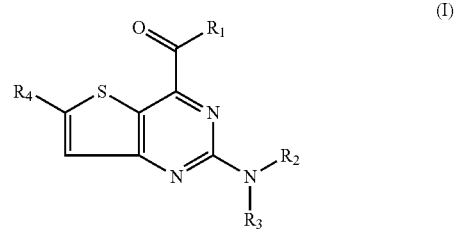

wherein
$R_1$ is optionally substituted aryl or an optionally substituted 5- or 6-membered heteroaryl ring;
$R_2$ and $R_3$ are independently selected from hydrogen, $C_1$-$C_8$ alkyl, $C_3$-$C_8$ cycloalkyl, $C_3$-$C_8$ cycloalkyl-($C_1$-$C_6$)-alkyl, aryl-($C_1$-$C_6$)-alkyl optionally substituted in the ring part thereof, a 5- or 6-membered monocyclic heterocyclic group optionally linked via a $C_1$-$C_6$ alkylene chain and optionally substituted in the ring part thereof, benzimidazol-2-yl-methyl, pyrid-3-yl-carbonyl, or (1-methyl-piperidin-4-yl)-carbonyl-methyl;
or $R_2$ and $R_3$ taken together with the nitrogen atom to which they are attached form an optionally substituted 5- or 6-membered ring;
$R_4$ is $C_1$-$C_3$ alkyl, $C_2$-$C_3$ alkenyl, —N(—$R_5$)—$R_6$, or optionally substituted heteroarylmethylamino; and $R_5$ and $R_6$ are independently selected from hydrogen or $C_1$-$C_3$ alkyl;

or $R_5$ and $R_6$ taken together with the nitrogen atom to which they are attached form an optionally substituted 4- to 6-membered saturated ring.

The active compounds of formula (I) are selective antagonists of the $A_{2B}$ receptor and are useful for the treatment, prevention and suppression of disorders mediated by the $A_{2B}$ receptor. Such disorders include nociception; asthma; chronic obstructive pulmonary disease (COPD); inflammatory diseases such as rheumatoid arthritis, multiple sclerosis, lupus, psoriasis and inflammatory bowel disease; diabetes mellitus or diabetes insipidus; diabetic retinopathy and cancer.

According to a further embodiment of the present invention there is provided the use of a compound of formula (I), or a pharmaceutically acceptable salt, hydrate, solvate, or prodrug thereof, in the manufacture of a medicament for the treatment of disorders mediated by the adenosine $A_{2B}$ receptor.

According to a further embodiment of the present invention there is provided a method of treatment of a disorder mediated by the $A_{2B}$ receptor comprising administration to a subject in need of such treatment an effective dose of the compound of formula (I), or a pharmaceutically acceptable salt, hydrate, solvate, or prodrug thereof.

According to a further embodiment of the present invention there is provided a pharmaceutical composition comprising a compound of formula (I), or a pharmaceutically acceptable salt, hydrate, solvate, or prodrug thereof, and a pharmaceutically acceptable carrier.

As used herein, the term "$(C_a$-$C_b)$alkyl" wherein a and b are integers refers to a straight or branched chain alkyl radical having from a to b carbon atoms. Thus when a is 1 and b is 6, for example; the term includes methyl, ethyl, n-propyl, iso-propyl, n-butyl, isobutyl, sec-butyl, t-butyl, n-pentyl and n-hexyl.

As used herein the term "divalent $(C_a$-$C_b)$alkylene radical" wherein a and b are integers refers to a saturated hydrocarbon chain having from a to b carbon atoms and two unsatisfied valences.

As used herein the term "$(C_a$-$C_b)$alkenyl" wherein a and b are integers refers to a straight or branched chain alkenyl moiety having from a to b carbon atoms having at least one double bond of either E or Z stereochemistry where applicable. The term includes, for example, vinyl, allyl, 1- and 2-butenyl and 2-methyl-2-propenyl.

As used herein the term "divalent $(C_a$-$C_b)$alkenylene radical" refers to a hydrocarbon chain having from a to b carbon atoms, at least one double bond, and two unsatisfied valences.

As used herein the term "cycloalkyl" refers to a saturated carbocyclic radical having from 3-8 carbon atoms and includes, for example, cyclopropyl, cyclobutyl, cyclopentyl, cyclohexyl, cycloheptyl and cyclooctyl.

As used herein the term "cycloalkenyl" refers to a carbocyclic radical having from 3-8 carbon atoms containing at least one double bond, and includes, for example, cyclopentenyl, cyclohexenyl, cycloheptenyl and cyclooctenyl.

As used herein the term "carbocyclic" refers to a mono- or bi-cyclic radical whose ring atoms are all carbon, and includes monocyclic aryl, cycloalkyl, and cycloalkenyl radicals, provided that no single ring present has more than 8 ring members. A "carbocyclic" group includes a mono-bridged or multiply-bridged cyclic alkyl group.

As used herein the term "aryl" refers to a mono-, bi- or tri-cyclic carbocyclic aromatic radical. Illustrative of such radicals are phenyl, biphenyl and napthyl.

As used herein the term "heteroaryl" refers to a mono-, bi- or tri-cyclic aromatic radical containing one or more heteroatoms selected from S, N and O. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl.

As used herein the unqualified term "heterocyclyl" or "heterocyclic" includes "heteroaryl" as defined above, and in particular refers to a mono-, bi- or tri-cyclic non-aromatic radical containing one or more heteroatoms selected from S, N and O, to groups consisting of a monocyclic non-aromatic radical containing one or more such heteroatoms which is covalently linked to another such radical or to a monocyclic carbocyclic radical, and to a mono-, bi- or tri-cyclic non-aromatic radical containing one or more heteroatoms selected from S, N and O which is mono-bridged or multiply-bridged. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyrimidinyl, morpholinyl, piperazinyl, indolyl, morpholinyl, benzfuranyl, pyranyl, isoxazolyl, benzimidazolyl, methylenedioxyphenyl, ethylenedioxyphenyl, maleimido and succinimido groups.

Unless otherwise specified in the context in which it occurs, the term "substituted" as applied to any moiety herein means substituted with at least one substituent, for example selected from $(C_1$-$C_6)$alkyl, $(C_1$-$C_6)$alkoxy, hydroxy, hydroxy$(C_1$-$C_6)$alkyl, mercapto, mercapto$(C_1$-$C_6)$alkyl, $(C_1$-$C_6)$alkylthio, halo (including fluoro and chloro), trifluoromethyl, trifluoromethoxy, nitro, nitrile (—CN), oxo, phenyl, —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —NH$_2$, —NHR$^A$, —NR$^A$R$^B$, —OCONH$_2$, —OCONHR$^A$, —OCONR$^A$R$^B$, —NHCOR$^A$, —NHCOOR$^A$, —NR$^B$COOR$^A$, —NHSO$_2$OR$^A$, —NR$^B$SO$_2$OR$^A$, —NHCONH$_2$, —NR$^A$CONH$_2$, —NHCONHR$^B$—NR$^A$CONHR$^B$, —NHCONR$^A$R$^B$, or —NR$^A$CONR$^A$R$^B$ wherein R$^A$ and R$^B$ are independently a $(C_1$-$C_6)$alkyl group, or R$^A$ and R$^B$ when attached to the same nitrogen may form a cyclic amino ring such as a morpholinyl, piperidinyl or piperazinyl ring. An "optional substituent" or "substituent" may be one of the foregoing substituent groups.

As used herein the term "salt" includes base addition, acid addition and quaternary salts. Compounds of the invention which are acidic can form salts, including pharmaceutically or veterinarily acceptable salts, with bases such as alkali metal hydroxides, e.g. sodium and potassium hydroxides; alkaline earth metal hydroxides e.g. calcium, barium and magnesium hydroxides; with organic bases e.g. N-ethyl piperidine, dibenzylamine and the like. Those compounds (I) which are basic can form salts, including pharmaceutically or veterinarily acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic and p-toluene sulphonic acids and the like.

For a review on suitable salts, see Handbook of Pharmaceutical Salts: Properties, Selection, and Use by Stahl and Wermuth (Wiley-VCH, Weinheim, Germany, 2002).

The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds with which the invention is concerned which may exist in one or more stereoisomeric form, because of the presence of asymmetric atoms or rotational restrictions, can exist as a number of stereoisomers with R or S stereochemistry at each chiral centre or as atropisomeres with R or S stereochemistry at each chiral axis. The invention includes all such enantiomers and diastereoisomers and mixtures thereof.

So-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in Design of Prodrugs by H. Bundgaard (Elsevier, 1985).

Also included within the scope of the invention are metabolites of compounds of formula (I), that is, compounds formed in vivo upon administration of the drug. Some examples of metabolites include
(i) where the compound of formula (I) contains a methyl group, an hydroxymethyl derivative thereof (—$CH_3$→—$CH_2OH$):
(ii) where the compound of formula (I) contains an alkoxy group, an hydroxy derivative thereof (—OR→—OH);
(iii) where the compound of formula (I) contains a tertiary amino group, a secondary amino derivative thereof (—$NR^1R^2$→—$NHR^1$ or —$NHR^2$);
(iv) where the compound of formula (I) contains a secondary amino group, a primary derivative thereof (—$NHR^1$→—$NH_2$);
(v) where the compound of formula (I) contains a phenyl moiety, a phenol derivative thereof (-Ph→-PhOH); and
(vi) where the compound of formula (I) contains an amide group, a carboxylic acid derivative thereof (—$CONH_2$→COOH).

Variable substituents present in compounds (I) will now be further defined. It is to be inferred in the further description that any disclosed substituent or substituent class may be present in any combination with any of the other disclosed substituent classes.

The Group $R_1$

In the compounds in accordance with the invention, $R_1$ is optionally substituted aryl or an optionally substituted 5- or 6-membered heteroaryl ring.

In a subclass of compounds with which the invention is concerned, $R_1$ is optionally substituted phenyl. When substituted, the phenyl ring preferably has one substituent, selected from methyl, methoxy, fluoro, chloro, or cyano.

In another subclass of compounds with which the invention is concerned, $R_1$ is an optionally substituted 5- or 6-membered heteroaryl ring. In such cases, the heteroaryl ring may be, for example, furan, thiophene, pyrrole, oxazole, thiazole, imidazole, or pyridine. Preferred substituents include methyl, ethyl, chloro, or bromo.

Presently, it is preferred that $R_1$ is optionally substituted thienyl, particularly thien-2-yl.

The Group —$N(R_2)$—$R_3$

In the compounds in accordance with the invention, $R_2$ and $R_3$ are independently selected from hydrogen, $C_1$-$C_6$ alkyl, $C_3$-$C_8$ cycloalkyl, $C_3$-$C_8$ cycloalkyl-($C_1$-$C_6$)-alkyl, aryl-($C_1$-$C_6$)-alkyl optionally substituted in the ring part thereof, a 5- or 6-membered monocyclic heterocyclic group optionally linked via a $C_1$-$C_6$ alkylene chain and optionally substituted in the ring part thereof, benzimidazol-2-yl-methyl, pyrid-3-yl-carbonyl, or (1-methyl-piperidin-4-yl)-carbonyl-methyl.

In a subclass of compounds with which the invention is concerned, $R_2$ is hydrogen and $R_3$ is a 5- or 6-membered monocyclic heterocyclic group optionally linked via a $C_1$-$C_6$ alkylene chain and optionally substituted in the ring part thereof. In such cases, the heterocyclic ring may be, for example, pyran, piperidine, morpholine, imidazole, pyridine, pyrimidine, pyrazine, or tetrazole. When present, methylene or ethylene is preferred for the $C_1$-$C_6$ alkylene chain.

In another subclass of compounds with which the invention is concerned, $R_2$ is hydrogen and $R_3$ is aryl-($C_1$-$C_6$)-alkyl optionally substituted in the ring part thereof. Phenyl is preferred for aryl, and when substituted, the phenyl ring preferably has one substituent, selected from methyl, ethyl, methoxy, or chloro. Methyl or ethyl is preferred for $C_1$-$C_6$ alkyl.

In a further subclass of compounds with which the invention is concerned, $R_2$ and $R_3$ taken together with the nitrogen atom to which they are attached form an optionally substituted 5- or 6-membered ring.

Presently, it is preferred that $R_2$ is hydrogen and $R_3$ is pyrid-3-ylmethyl.

The Group $R_4$

In the compounds in accordance with the invention, $R_4$ is $C_1$-$C_3$ alkyl, $C_2$-$C_3$ alkenyl, —N(—$R_5$)—$R_6$, or optionally substituted heteroarylmethylamino.

In a subclass of compounds with which the invention is concerned, $R_4$ is $C_1$-$C_3$ alkyl, preferably ethyl.

In another subclass of compounds with which the invention is concerned, $R_4$ is $C_2$-$C_3$ alkenyl, preferably ethenyl.

In a further subclass of compounds with which the invention is concerned, $R_4$ is optionally substituted heteroarylmethylamino. In such cases, heteroaryl represents a 5- or 6-membered monocyclic heteroaryl ring, with pyridyl preferred, particularly pyrid-3-yl.

In yet another subclass of compounds with which the invention is concerned, $R_4$ is amino, mono-($C_1$-$C_3$-alkyl)amino, or di-($C_1$-$C_3$-alkyl)amino. In a further subclass of compounds with which the invention is concerned, $R_4$ is —N(—$R_5$)—$R_6$ wherein $R_5$ and $R_6$ taken together with the nitrogen atom to which they are attached form an optionally substituted 4- to 6-membered saturated ring. In such cases, —N(—$R_5$)—$R_6$ includes azetidin-1-yl, pyrrolidin-1-yl and piperidin-1-yl, with azetidin-1-yl and pyrrolidin-1-yl preferred, particularly azetidin-1-yl.

Presently, it is preferred that $R_4$ is amino, methylamino, ethylamino, dimethylamino, ethyl, ethenyl, or pyrid-3-ylmethylamino.

It is particularly preferred that $R_4$ is amino or methylamino.

Specific compounds with which the invention is concerned include those of the Examples.

The present invention may be employed in respect of a human or animal subject, more preferably a mammal, more preferably a human subject.

As used herein, the term "treatment" as used herein includes prophylactic treatment.

The compound of formula (I) may be used in combination with one or more additional drugs useful in the treatment of the disorders mentioned above, the components being in the same formulation or in separate formulations for administration simultaneously or sequentially.

It will be understood that the specific dose level for any particular patient will depend upon a variety of factors including the activity of the specific compound employed, the age, body weight, general health, sex, diet, time of administration, route of administration, rate of excretion, drug combination and the causative mechanism and severity of the particular disease undergoing therapy. In general, a suitable dose for orally administrable formulations will usually be in the range of 0.1 to 3000 mg, once, twice or three times per day, or the equivalent daily amount administered by infusion or other routes. However, optimum dose levels and frequency of dosing will be determined by clinical trials as is conventional in the art.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to the one skilled in the art. Typical literature sources are "Advanced organic chemistry", 4$^{th}$ Edition (Wiley), J March, "Comprehensive Organic Transformation", 2$^{nd}$ Edition (Wiley), R. C. Larock, "Handbook of Heterocyclic Chemistry", 2$^{nd}$ Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstracts" or "Beilstein". Such literature methods include those of the preparative Examples herein, and methods analogous thereto.

Scheme 1 represents a method known in the art of organic chemistry in general, by which the compounds of the present invention may be prepared:

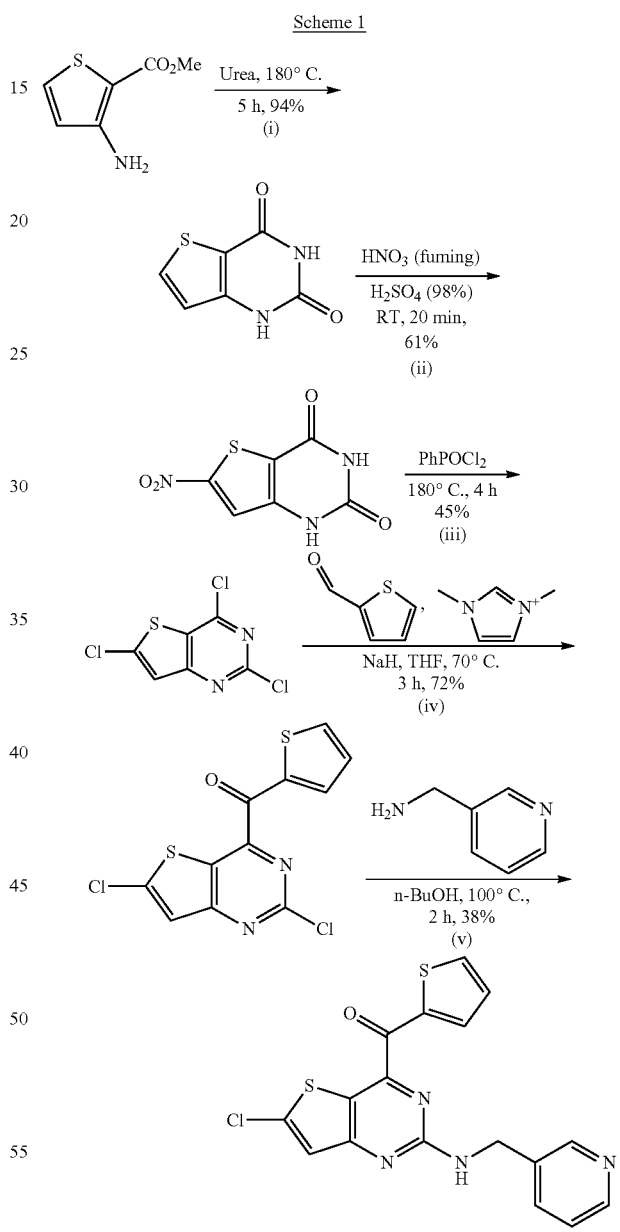

EXAMPLES

The following examples illustrate the preparation of specific compounds of the invention and are not intended to be limiting of the full scope of the invention.

Examples 1 to 5 relate to the method indicated in Scheme 1.

Preparative Example 1

1H-Thieno[3,2-d]pyrimidine-2,4-dione

A solid mixture of methyl-3-aminothiophene-2-carboxylate (76 g, 480 mmol) and urea (189 g, 3140 mmol) was heated, with stirring, to 180° C. for 5 h. The mixture was cooled to 90° C. and water (1000 ml) added. After stirring at room temperature for 16 h, a cream coloured solid was filtered and washed twice with further water. The solid was dried in vacuo at 40° C. to give the title compound in 94% yield, >95% purity. LC-MS m/z=169.0 [M+H]$^+$; RT=1.29 min; LC-MS method 2. $^1$H NMR: $\delta_H$ (400 MHz, D$_6$-DMSO) 6.90 (1H, d, J=5.5 Hz), 8.04 (1H, d, J=5.5 Hz), 11.10-11.80 (2H, b).

Preparative Example 2

6-Nitro-1H-thieno[3,2-d]pyrimidine-2,4-dione

A stirred mixture of concentrated sulphuric acid (98%, 270 ml) and fuming nitric acid (270 ml) at 0° C. was treated portionwise with Example 1 (90 g, 530 mmol). Upon complete dissolution, stirring was continued at room temperature for a further 20 min. The solution was added slowly to vigorously stirred ice/water (2000 ml). After 30 min stirring at room temperature, a yellow solid was filtered, washed with water and dried in vacuo at 40° C. to give the title compound in 61% yield, >95% purity. LC-MS m/z=251.0 [M+H]$^+$; RT=2.92; LC-MS method 1. $^1$H NMR: $\delta_H$ (400 MHz, D$_6$-DMSO) 7.66 (1H, s), 11.71 (1H, b), 11.79 (1H, b).

Preparative Example 3

2,4,6-Trichloro-thieno[3,2-d]pyrimidine

A suspension of Example 2 (70 g, 330 mmol) in phenylphosphonic dichloride (320 ml, 2310 mmol) was heated, with stirring, to 180° C. for 4 h. The mixture was cooled to 100° C. and transferred slowly onto vigorously stirred ice/water (2500 ml). After 2 h stirring at room temperature, a tan solid was filtered and dried in vacuo at 40° C. The solid was dissolved in the minimum volume of tetrahydrofuran and passed over a short pad of silica using ethyl acetate as an eluent. The filtrate was reduced in vacuo and the residue re-crystallised from iso-hexane:ethyl acetate (10:1) to give the title compound in 45% yield, >95% purity. LC-MS m/z=239.0 [M+H]$^+$; RT=3.39 min; LC-MS method 1. $^1$H NMR: $\delta_H$ (400 MHz, D$_6$-DMSO) 7.94 (1H, s)

Preparative Example 4

(2,6-Dichloro-thieno[3,2-d]pyrimidin-4-yl)-thiophen-2-yl-methan-one

A stirred solution of Example 3 (6.86 g, 29 mmol) in tetrahydrofuran (200 ml) was treated with dimethylimidazolium iodide (2.13 g, 9.6 mmol), thiophene-2-carbaldehyde (3.19 ml, 35 mmol) and sodium hydride (1.51 g, 38 mmol). The mixture was first stirred at room temperature for 25 min and then heated, with stirring, to 70° C. for 3 h. The reaction mixture was cooled to room temperature and reduced in vacuo. The residue was partitioned between water and dichloromethane. The organic fraction was separated, dried over sodium sulfate and reduced in vacuo. Trituration with methanol gave the title compound in 72% yield, 95% purity. LC-MS m/z=279.1 [M+H]$^+$; RT=3.77 min; LC-MS method 1. $^1$H NMR: $\delta_H$ (400 MHz, D$_6$-DMSO) 7.40-7.42 (1H, m), 7.95 (1H, s), 8.31 (1H, d, J=4.5 Hz), 8.61 (1H, d, J 4.5 Hz).

Preparative Example 5

{6-Chloro-2-[(pyridin-3-ylmethyl)-amino]-thieno[3,2-d]pyrimidin-4-yl}-thiophen-2-yl-methanone A stirred solution of Example 4 (5 g, 16 mmol) in n-butanol (120 ml) was treated with 3-picolylamine (8.1 ml, 80 mmol) and heated to 100° C. for 2 h. The reaction mixture was cooled to room temperature, reduced in vacuo and the residue purified by silica gel (100 g) column chromatography (3% MeOH/DCM) affording the title compound in 38% yield, >95% purity. LC-MS m/z=387.0 [M+H]$^+$; RT=3.30 min; LC-MS method 1.
$^1$H NMR: $\delta_H$ (400 MHz, D$_6$-DMSO) 4.73 (2H, b), 7.31-7.36 (2H, m), 7.47 (1H, s), 7.80 (1H, d, J 6.0 Hz), 8.20-8.28 (2H, m), 8.44 (1H, d, J 6.0 Hz), 8.64 (1H, bd).

Example 6

{6-Methylamino-2-[(pyridin-3-ylmethyl)-amino]-thieno[3,2-d]pyrimidin-4-yl}-thiophen-2-yl-methanone

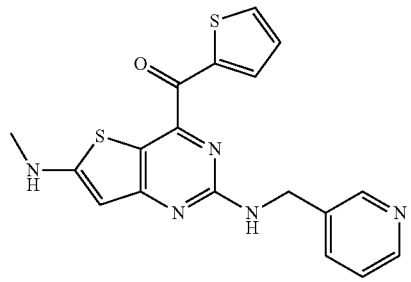 [SMILES: CNc1cc2nc(NCc3cccnc3)nc(C(=O)c3cccs3)c2s1]

A stirred solution of Example 5 (0.4 g, 1 mmol) in dimethyl acetamide (10 ml) was treated with methylamine (2.0M in MeOH, 4.96 ml, 1.10 mmol). The solution was heated to 150° C. in a sealed tube for 1 h. The solution was cooled to room temperature and slowly poured onto stirred iced water (100 ml). After 15 min stirring, a light orange solid was filtered. Recrystallisation from hot ethyl acetate gave the title compound in 58% yield, >95% purity. LC-MS m/z=382.0 [M+H]$^+$; RT=2.73; LC-MS method 1. $^1$H NMR: $\delta_H$ (400 MHz, D$_6$-DMSO) 2.89 (3H, d, J 5.0 Hz), 4.67 (2H, d, J 6.0 Hz), 5.81 (1H, s), 7.23 (1H, t, J 4.5 Hz), 7.77 (1H, d, J 8.0 Hz), 7.96 (1H, b), 8.09 (1H, d, J=5.0 Hz), 8.41 (1H, d, J=5.0 Hz), 8.36-8.50 (1H, b), 8.61 (1H, bd)

Example 7

{6-dimethylamino-2-[(pyridine-3-ylmethyl)-amino]-thieno[3,2-d]pyrimidin-4-yl}-thiophen-2-yl-methanone

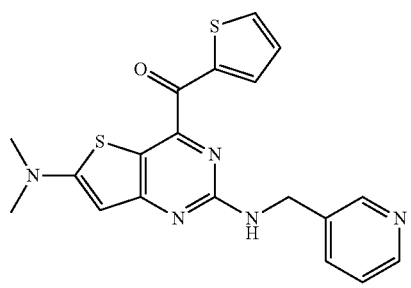 [SMILES: CN(C)c1cc2nc(NCc3cccnc3)nc(C(=O)c3cccs3)c2s1]

A stirred solution of Example 5 (0.02 g, 0.052 mmol) in dimethylacetamide (1.5 ml) was treated with dimethylamine (2.0M in THF, 0.52 mmol). The solution was heated to 170° C. for 30 min in a microwave reactor. The cooled solution was poured onto stirred iced water (20 ml). After 15 min stirring, an orange solid was filtered. Recrystallisation from hot ethyl acetate gave the title compound in 42% yield, >95% purity. LC-MS m/z=396.0 [M+H]$^+$; RT=2.97; LC-MS method 1. $^1$H NMR: $\delta_H$ (400 MHz, D$_6$-DMSO) 3.13 (6H, s), 4.68 (2H, bd), 5.91 (1H, s), 7.26-8.61 (8H, m).

Example 8

{6-Ethylamino-2-[(pyridin-3-ylmethyl)-amino]-thieno[3,2-d]pyrimidin-4-yl}-thiophen-2-yl-methanone

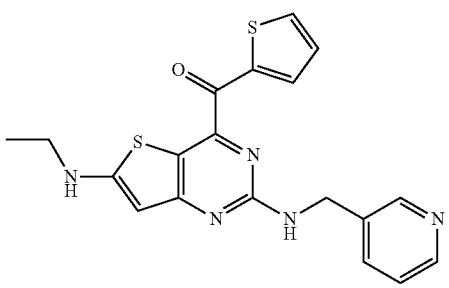 [SMILES: CCNc1cc2nc(NCc3cccnc3)nc(C(=O)c3cccs3)c2s1]

A stirred solution of Example 5 (0.025 g, 0.065 mmol) in dimethyl acetamide (1.5 ml) was treated with ethylamine (2.0M in THF, 0.65 mmol). The solution was heated to 170° C. for 30 min in a microwave reactor. The cooled solution was poured on to aqueous HCl solution (2.5M, 25 ml). The aqueous solution was washed with ethylacetate (50 ml) and basified (pH 9) using aqueous sodium hydroxide solution (5M). The title compound was filtered as an orange solid in 40% yield, >90% purity. LC-MS m/z=396.0 [M+H]$^+$; RT=2.78; LC-MS method 1. $^1$H NMR: $\delta_H$ (400 MHz, D$_6$-DMSO) 1.21 (3H, t, J 7.0 Hz), 3.22-3.33 (2H, m), 4.68 (2H, bd), 5.82 (1H, s), 7.23-8.63 (11H, m).

Example 9

{6-Amino-2-[(pyridin-3-ylmethyl)-amino]-thieno[3,2-d]pyrimidin-4-yl}-thiophen-2-yl-methanone

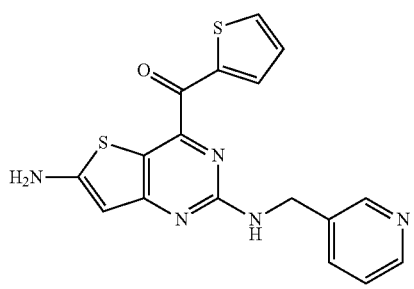 [SMILES: Nc1cc2nc(NCc3cccnc3)nc(C(=O)c3cccs3)c2s1]

A stirred solution of Example 5 (0.055 g, 0.143 mmol) in dimethylacetamide (2 ml) was treated with 3,4-dimethoxybenzylamine (0.22 ml, 1.43 mmol). The solution was heated to 170° C. for 30 min in a microwave reactor. The cooled solution was reduced in vacuo and taken up in neat trifluoroacetic acid (3 ml). The mixture was stirred at 70° C. for 48 h, cooled and reduced in vacuo. The residue was taken up in ethylacetate (25 ml), washed with saturated sodium bicarbonate solution (15 ml), dried over sodium sulfate and reduced in vacuo. Silica gel (10 g) column chromatography (10% MeOH in EtOAc) afforded the title compound as an orange solid in 9% yield, >95% purity. LC-MS m/z=368.0 [M+H]$^+$; RT=2.58; LC-MS method 1. $^1$H NMR: $\delta_H$ (400 MHz, D$_6$-DMSO) 4.67 (2H, bd), 5.81 (1H, s), 7.23-7.25 (1H, m), 7.33-7.36 (1H, m), 7.51 (2H, b), 7.79 (1H, bd), 8.09 (1H, bd), 8.38-8.62 (4H, bm)

Example 10

{2-[(Pyridin-3-ylmethyl)-amino]-6-vinyl-thieno[3,2-d]pyrimidin-4-yl}-thiophen-2-yl-methanone

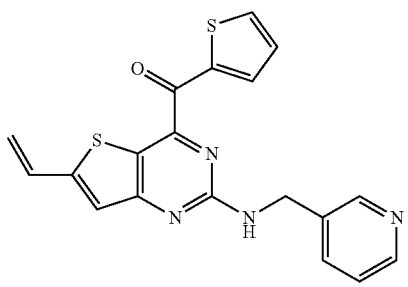 [SMILES: C=Cc1cc2nc(NCc3cccnc3)nc(C(=O)c3cccs3)c2s1]

A stirred solution of Example 5 (0.05 g, 0.13 mmol) in tetrahydrofuran (3 ml) at room temperature was treated with tris[di(benzylidene)acetone]palladium (0) (0.006 g, 0.0065 mmol), tri-tert-butylphosphine (0.01 ml, 0.04 mmol), tributylvinyltin (0.06 ml, 0.0.195 mmol), and caesium carbonate (0.046 g, 0.14 mmol). The mixture was heated to 140° C. for 20 min in a microwave reactor. The cooled reaction mixture was poured onto aqueous HCl (2.5M, 25 ml), washed with ethylacetate, and basified (pH9) using aqueous sodium hydroxide solution (5M). The aqueous phase was extracted with ethyl acetate (2×30 ml). Combined extracts were dried over sodium sulfate and reduced in vacuo. Silica gel (10 g) column chromatography (ethyl acetate) afforded the title compound as a yellow solid in 51% yield, >95% purity. LC-MS m/z=379.0 [M+H]$^+$; RT=3.15; LC-MS method 1. $^1$H NMR: $\delta_H$ (400 MHz, D$_6$-DMSO) 4.73 (2H, b), 5.57 (1H, d, J 10.5 Hz), 6.00 (1H, d, J 17.5 Hz), 7.06-7.14 (1H, m), 7.29-7.35 (3H, m), 7.79 (1H, d, J 8.0 Hz), 8.11-8.19 (2H, m), 8.43 (1H, d, J 4.5 Hz), 8.64 (1H, bd), 8.43-8.64 (1H, b)

Example 11

{6-Ethyl-2-[(pyridin-3-ylmethyl)-amino]-thieno[3,2-d]pyrimidin-4-yl}-thiophen-2-yl-methanone

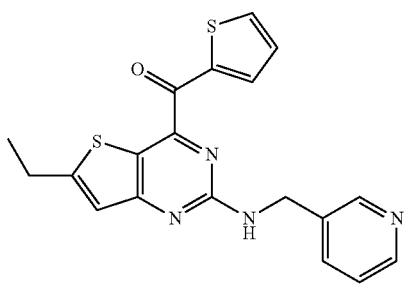 [SMILES: CCc1cc2nc(NCc3cccnc3)nc(C(=O)c3cccs3)c2s1]

A stirred solution of Example 10 (0.025 g, 0.066 mmol) in ethanol (5 ml) was treated with palladium/activated carbon (10%, 0.0025 g) and HCl (1.25M in MeOH, 0.19 mmol). The Flask was thoroughly evacuated and placed under 1 atmosphere of hydrogen gas. The mixture was stirred under hydrogen overnight at room temperature, evacuated and filtered through celite. The filtrate was reduced in vacuo to give the title compound as a yellow solid in 70% yield, >95% purity. LC-MS m/z=381.0 [M+H]$^+$; RT=3.19; LC-MS method 1. $^1$H NMR: $\delta_H$ (400 MHz, D$_6$-DMSO) 1.33 (3H, t, J 7.5 Hz), 2.95 (2H, q, J 7.5 Hz), 4.71 (2H, b), 7.08 (1H, s), 7.28-7.35 (2H, m), 7.78 (1H, d, J 8.0 Hz), 8.06 (1H, bt), 8.17 (1H, d, J 4.5 Hz), 8.43 (1H, d, J 4.5 Hz), 8.63 (1H, bd), 8.40-8.65 (1H, b).

Example 12

{6-(3-picolylamino)-2-[(pyridin-3-ylmethyl)-amino]-thieno[3,2-d]pyrimidin-4-yl}-thiophen-2-yl-methanone

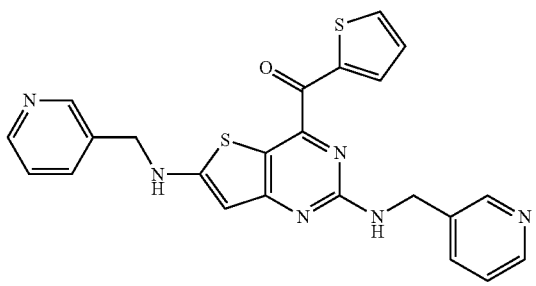 [SMILES: O=C(c1cccs1)c1nc(NCc2cccnc2)nc2cc(NCc3cccnc3)sc12]

A stirred solution of Example 5 (0.02 g, 0.052 mmol) in dimethylacetamide (1.5 ml) was treated with 3-picolylamine (0.105 ml, 1.04 mmol). The solution was heated to 170° C. for 30 min in a microwave reactor. The cooled solution was poured on to aqueous HCl solution (2.5M, 25 ml). The aqueous solution was washed with ethylacetate (50 ml) and basified (pH 9) using aqueous sodium hydroxide solution (5M). The title compound was filtered as an orange solid in 59% yield, >95% purity. LC-MS m/z=459.0 [M+H]$^+$; RT=2.67; LC-MS method 1. $^1$H NMR: $\delta_H$ (400 MHz, D$_6$-DMSO) 4.51 (2H, d, J 5.5 Hz), 4.66 (2H, bd), 5.93 (1H, s), 7.23-7.41 (3H, m), 7.55 (1H, bt), 7.75-7.81 (2H, m), 8.10 (1H, d, J=5.0 Hz), 8.40-8.63 (6H, m).

General Procedures

All reagents obtained from commercial sources were used without further purification. Anhydrous solvents were obtained from commercial sources and used without further drying. Flash chromatography was performed with pre-packed silica-gel cartridges (Strata Si-1; 61 Å, Phenomenex, Cheshire, UK or IST Flash II, 54 Å, Argonaut, Hengoed, UK). Thin layer chromatography was conducted with 5×10 cm plates coated with Merck Type 60 F$_{254}$ silica-gel. Microwave heating was performed with a Biotage Initiatorr™ 2.0 instrument.

The compounds of the present invention were characterized by liquid chromatography-mass spectroscopy (LC-MS) using the following methods.

LC-MS Method 1
Instrument: Waters 2695 pump and 2700 sample manager
Waters ZQ2000, M/z range 100 to 900 amu
Column: Gemini 5 µm, C18 110A, 30 mm×2 mm from Phenomenex. Pt no 00A-4435-B0
Temperature: Ambient
Mobile Phase: A—Water+10 mMol/ammonium formate+0.04% (v/v) formic acid at pH ca 3.5
B–100% Acetonitrile+0.04% (v/v) formic acid
Injection Volume 10 uL
Gradient:

| Time (min) | Solvent A (%) | Solvent B (%) | Flow (cm$^3$min$^{-1}$) |
|---|---|---|---|
| −0.8 (Equil) | 95 | 5 | 1.0 |
| 0 | 95 | 5 | 0.8 |
| 0.25 | 95 | 5 | 0.8 |
| 2.50 | 5 | 95 | 0.8 |
| 4.0 | 5 | 95 | 0.8 |
| 5 | 5 | 95 | 1.0 |
| 5.2 | 95 | 5 | 1.0 |

Detection: UV detection from 220 to 400 nm (1:3 split MS to UV)

LC-MS Method 2
Instrument: Waters 2695 pump and 2700 sample manager
Waters ZQ2000, M/z range 100 to 900 amu
Column: Gemini 5 µm, C18 110A, 30 mm×2 mm from Phenomenex. Pt no 00A-4435-B0
Temperature: Ambient
Mobile Phase: A—Water+10 mMol/ammonium formate+0.04% (v/v) formic acid at pH ca 3.5
B—100% Acetonitrile+0.04% (v/v) formic acid
Injection Volume 5 uL
Gradient:

| Time (min) | Solvent A (%) | Solvent B (%) | Flow (cm$^3$min$^{-1}$) |
|---|---|---|---|
| 0 | 95 | 5 | 0.4 |
| 0.5 | 95 | 5 | 0.4 |
| 3 | 5 | 95 | 0.4 |
| 6 | 5 | 95 | 0.4 |
| 6.5 | 95 | 5 | 0.4 |

Detection: UV detection from 220 to 400 nm

Nuclear magnetic resonance (NMR) analysis was performed with a Bruker DPX400 spectrometer and proton NMR spectra were measured at 400 MHz. The spectral reference was the known chemical shift of the solvent. Proton NMR data is reported as follows: chemical shift ($\delta$) in ppm, followed by the integration, the multiplicity (where s=singlet, d=doublet, t=triplet, q=quartet, p=pentet, m=multiplet, dd=doublet of doublets and br=broad), and the coupling constant rounded to the nearest 0.1 Hz.

Some compounds of the invention were purified by preparative HPLC. These were performed on a Waters Fraction-Lynx MS autopurification system, with a Gemini® 5 µm C18(2), 100 mm×20 mm i.d. column from Phenomenex, running at a flow rate of 20 cm$^3$ min$^{-1}$ with UV diode array detection (210-400 nm) and mass-directed collection. Gradients used for each compound are shown in Table 1.

At pH 4: solvent A=10 mM ammonium acetate in HPLC grade water+0.08% v/v formic acid. Solvent B=95% v/v HPLC grade acetonitrile+5% v/v solvent A+0.08% v/v formic acid.

At pH 9: solvent A=10 mM ammonium acetate in HPLC grade water+0.08% v/v ammonia solution. Solvent B=95% v/v HPLC grade acetonitrile+5% v/v solvent A+0.08% v/v ammonia solution.

The mass spectrometer was a Waters Micromass ZQ2000 spectrometer, operating in positive or negative ion electrospray ionisation modes, with a molecular weight scan range of 150 to 1000.

TABLE 1

Preparative HPLC gradients

| | % Solvent B for Example No. | | | | |
|---|---|---|---|---|---|
| Time (min) | 4, 5 and 14 | 6, 8, 11, 12, 15-18, 21 and 26 | 19, 20 and 23 | 2, 3, 9, 10 and 13 | 24 | 27 |
| 0.0 | 5 | 5 | 5 | 5 | 5 | 5 |
| 0.5 | 6 | 15 | 15 | 30 | 10 | 25 |
| 7.0 | 25 | 30 | 40 | 40 | 20 | 50 |
| 7.5 | 95 | 95 | 95 | 95 | 95 | 95 |
| 9.5 | 95 | 95 | 95 | 95 | 95 | 95 |
| 10 | 5 | 5 | 5 | 5 | 5 | 5 |

IUPAC chemical names were generated using AutoNom Standard.

Assay Description

The use of a Fluorometric Imaging Plate Reader (FLIPR) to measure calcium flux in Adenosine-receptor expressing cells is a well-established technique. In this assay calcium flux is triggered by receptor activation and measured through the fluorescence of an incorporated calcium-sensitive dye. The potencies shown were determined using expressed human adenosine $A_{2B}$ receptors in mammalian cell lines. Selectivity values were obtained by using mammalian cell lines expressing the human adenosine $A_1$, $A_{2A}$ and $A_3$ receptors. Compound potency was determined from dose response curves and is reported as an $IC_{50}$ value.

All examples were tested for activity in the functional assay described above. The resulting experimental data for each example are given in Table 2 below.

All examples demonstrate unexpected selectivity for binding at the $A_{2B}$ receptor versus the $A_{2A}$ receptor. The binding affinity of the examples is of magnitude 12 to 198-fold higher for the $A_{2B}$ receptor versus the $A_{2A}$ receptor, whilst also retaining selectivity over the $A_1$ and $A_3$ sub-types.

TABLE 2

| Example No. | A1 Kb Mean (nM) | A2a Kb Mean (nM) | A2b Kb Mean (nM) | A3 Kb Mean (nM) | A1/A2b | A2a/A2b | A3/A2b |
|---|---|---|---|---|---|---|---|
| 6 | 57.6 | 276.8 | 1.4 | 22.9 | 41 | 198 | 16 |
| 7 | 19.4 | 318.3 | 6.5 | 130.3 | 3 | 49 | 20 |
| 8 | 118.3 | 726.3 | 6.7 | 37.3 | 18 | 109 | 6 |
| 9 | 1103.5 | 1400.0 | 7.1 | 233.1 | 155 | >196 | 33 |
| 10 | 161.3 | 3750.0 | 52.3 | 746.7 | 3 | >71 | 14 |
| 11 | 216.0 | 3750.0 | 36.7 | 360.8 | 6 | >102 | 10 |
| 12 | 256.2 | 828.3 | 68.9 | 308.3 | 4 | 12 | 4 |

The invention claimed is:

1. A compound of formula (I) or a pharmaceutically acceptable salt thereof:

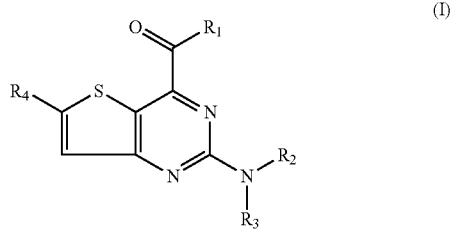

(I)

wherein
$R_1$ is optionally substituted aryl or an optionally substituted 5- or 6-membered heteroaryl ring;
$R_2$ and $R_3$ are independently selected from hydrogen, $C_1$-$C_6$ alkyl, $C_3$-$C_8$ cycloalkyl, $C_3$-$C_8$ cycloalkyl-($C_1$-$C_6$)-alkyl, aryl-($C_1$-$C_6$)-alkyl optionally substituted in the ring part thereof, a 5- or 6-membered monocyclic heterocyclic group optionally linked via a $C_1$-$C_6$ alkylene chain and optionally substituted in the ring part thereof, benzimidazol-2-yl-methyl, pyrid-3-yl-carbonyl, or (1-methyl-piperidin-4-yl)-carbonyl-methyl;
or $R_2$ and $R_3$ taken together with the nitrogen atom to which they are attached form an optionally substituted 5- or 6-membered ring;
$R_4$ is $C_1$-$C_3$ alkyl, $C_2$-$C_3$ alkenyl, —N(—$R_5$)—$R_6$, or optionally substituted heteroarylmethylamino; and
$R_5$ and $R_6$ are independently selected from hydrogen or $C_1$-$C_3$ alkyl;
or $R_5$ and $R_6$ taken together with the nitrogen atom to which they are attached form an optionally substituted 4- to 6-membered saturated ring.

2. A compound as claimed in claim 1 wherein $R_1$ is an optionally substituted 5- or 6-membered heteroaryl ring.

3. A compound as claimed in claim 1 wherein $R_1$ is an optionally substituted 5-membered heteroaryl ring.

4. A compound as claimed in claim 1 wherein $R_1$ is optionally substituted thienyl.

5. A compound as claimed in claim 4 wherein $R_1$ is thienyl optionally substituted by fluoro, chloro, bromo, cyano, methyl, trifluoromethyl, ethyl, hydroxyl, hydroxymethyl, or hydroxyethyl.

6. A compound as claimed in claim 1 wherein $R_1$ is thien-2-yl.

7. A compound as claimed in claim 1 wherein $R_2$ is hydrogen, or a 5- or 6-membered monocyclic heterocyclic group optionally linked via a $C_1$-$C_6$ alkylene chain and optionally substituted in the ring part thereof.

8. A compound as claimed in claim 7 wherein $R_2$ is hydrogen.

9. A compound as claimed in claim 7 wherein $R_2$ is an optionally substituted 5- or 6-membered monocyclic heteroaryl group linked via a $C_1$-$C_6$ alkylene chain.

10. A compound as claimed in claim 7 wherein $R_2$ is a 5- or 6-membered monocyclic heteroaryl group linked via a $C_1$-$C_6$ alkylene chain and optionally substituted in the ring part thereof by fluoro, chloro, bromo, cyano, methyl, trifluoromethyl, ethyl, hydroxyl, hydroxymethyl, or hydroxyethyl.

11. A compound as claimed in claim 1 wherein $R_3$ is hydrogen, or a 5- or 6-membered monocyclic heterocyclic group optionally linked via a $C_1$-$C_6$ alkylene chain and optionally substituted in the ring part thereof.

12. A compound as claimed in claim 11 wherein $R_3$ is an optionally substituted 5- or 6-membered monocyclic heteroaryl group linked via a $C_1$-$C_6$ alkylene chain.

13. A compound as claimed in claim 11 wherein $R_3$ is a 5- or 6-membered monocyclic heteroaryl group linked via a $C_1$-$C_6$ alkylene chain and optionally substituted in the ring part thereof by fluoro, chloro, bromo, cyano, methyl, trifluoromethyl, ethyl, hydroxyl, hydroxymethyl, or hydroxyethyl.

14. A compound as claimed in claim 1 wherein $R_4$ is amino.

15. A compound as claimed in claim 1 wherein $R_4$ is mono $C_1$-$C_3$ alkylamino.

16. A compound as claimed in claim 15 wherein $R_4$ is methylamino.

17. A compound as claimed in claim 15 wherein $R_4$ is ethylamino.

18. A compound as claimed in claim 1 wherein $R_4$ is $C_1$-$C_3$ alkyl.

19. A compound as claimed in claim 18 wherein $R_4$ is ethyl.

20. A compound of formula (II) or a pharmaceutically acceptable salt thereof:

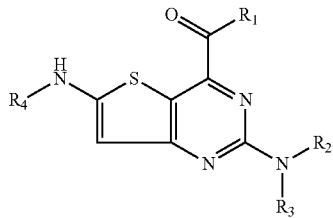

(II)

wherein
$R_1$ is optionally substituted aryl or an optionally substituted 5- or 6-membered heteroaryl ring;
$R_2$ and $R_3$ are independently selected from hydrogen, $C_1$-$C_6$ alkyl, $C_3$-$C_8$ cycloalkyl, $C_3$-$C_8$ cycloalkyl-($C_1$-$C_6$)-alkyl, aryl-($C_1$-$C_6$)-alkyl optionally substituted in the ring part thereof, a 5- or 6-membered monocyclic heterocyclic group optionally linked via a $C_1$-$C_6$ alkylene chain and optionally substituted in the ring part thereof, benzimidazol-2-yl-methyl, pyrid-3-yl-carbonyl, or (1-methyl-piperidin-4-yl)-carbonyl-methyl;
or $R_2$ and $R_3$ taken together with the nitrogen atom to which they are attached form an optionally substituted 5- or 6-membered ring; and
$R_4$ is hydrogen or $C_1$-$C_3$ alkyl.

21. A compound as claimed in claim 20 wherein $R_1$ is thien-2-yl.

22. A compound as claimed in claim 20 wherein $R_2$ is hydrogen and $R_3$ is pyrid-3-ylmethyl.

23. A compound as claimed in claim 20 wherein $R_4$ is hydrogen or methyl.

24. A pharmaceutical composition comprising a compound as claimed in claim 1 and a pharmaceutically acceptable carrier.

25. A compound as claimed in claim 1 wherein $R_1$ is thien-2-yl, $R_2$ is hydrogen, and $R_3$ is pyrid-3-ylmethyl.

* * * * *